United States Patent [19]

Smith

[11] Patent Number: 5,373,581
[45] Date of Patent: Dec. 13, 1994

[54] AUTOMOBILE PLUG-IN AIR FRESHENER WITH ROTATABLE SWITCH AND VAPORIZER

[76] Inventor: James S. Smith, P.O. Box 3170, Leesburg, Va. 22075

[21] Appl. No.: 155,383

[22] Filed: Nov. 22, 1993

[51] Int. Cl.⁵ .......................... F22B 1/28; A61L 9/02; A01M 1/20; F23Q 2/32
[52] U.S. Cl. .................... 392/390; 219/202; 219/267; 261/142; 261/DIG. 65; 392/392; 422/125; 422/128
[58] Field of Search .............. 392/386, 390, 391, 392, 392/394, 403–407; 219/202, 267; 261/142, DIG. 65; 422/125, 128

[56] References Cited

U.S. PATENT DOCUMENTS

| | | | |
|---|---|---|---|
| D. 306,644 | 3/1990 | Luthy | 261/142 X |
| D. 314,044 | 1/1991 | Montari | 261/142 X |
| 2,931,880 | 4/1960 | Yaffe | 392/390 |
| 3,872,280 | 3/1975 | Van Dalen | 392/390 |
| 4,214,146 | 7/1980 | Schimanski | 392/390 |
| 4,391,781 | 7/1983 | van Lit | 392/390 X |
| 4,725,712 | 2/1988 | Schroeder | 392/390 |
| 4,731,520 | 3/1988 | Glucksman et al. | 392/390 |
| 4,849,606 | 7/1989 | Martens, III et al. | 392/390 |

FOREIGN PATENT DOCUMENTS 2062199 5/1981 United Kingdom ............... 392/390

Primary Examiner—Anthony Bartis
Attorney, Agent, or Firm—Michael J. Colitz, Jr.

[57] ABSTRACT

An automobile plug-in air freshener with a main body portion in a cylindrical configuration having an open outboard end and a closed inboard end and pluggable into an electrical cigarette lighter socket of a vehicle. An extension portion has a cone shaped interior component rotatably positioned outboardly of the open end of the cylinder with an interior edge in a cylindrical configuration positioned rotatably in the outboard end of the main body portion with an exterior component in a rectangular configuration constituting a housing with an opened inboard end and louvers at the outboard end and a slot along an upper intermediate extent. A generally planar refill container in a rectangular configuration is removably positionable within the slot of the rectangular housing, the refill container having a fragrance therein activated by heat. A heating element is located within the main body portion adjacent to the outboard open end is energized by a switch actuated by rotation of the extension portion to heat the fragrance within the refill cartridge for disseminating a fragrance and freshening the adjacent air.

2 Claims, 3 Drawing Sheets

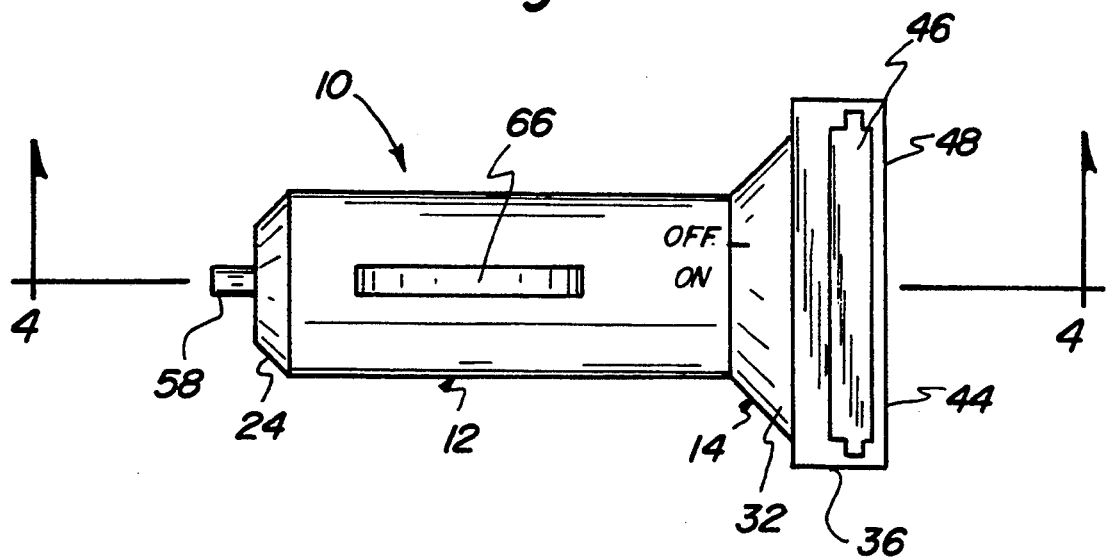
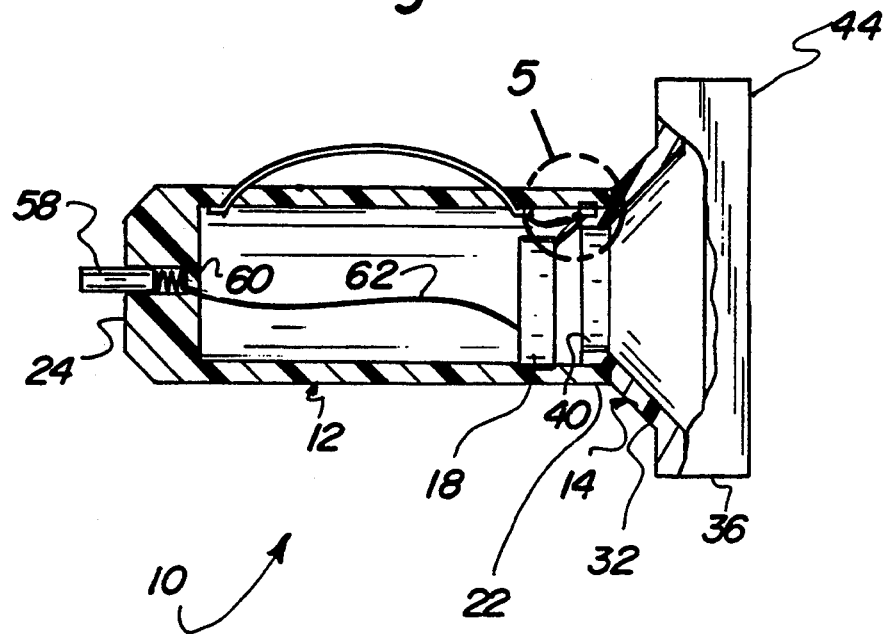

5,373,581

AUTOMOBILE PLUG-IN AIR FRESHENER WITH ROTATABLE SWITCH AND VAPORIZER

BACKGROUND OF THE INVENTION

1. Field of the Invention

The present invention relates to automobile plug-in air fresheners and more particularly pertains to freshening the air of vehicles with devices plugged into a cigarette lighter.

2. Description of the Prior Art

The use of air fresheners is known in the prior art. More specifically, air fresheners heretofore devised and utilized for the purpose of freshening air are known to consist basically of familiar, expected, and obvious structural configurations, notwithstanding the myriad of designs encompassed by the crowded prior art which has been developed for the fulfillment of countless objectives and requirements.

The prior art discloses a large number of devices used for freshening air. By way of example, U.S. Pat. No. Des. 306,644 to Luthy discloses a design for an electric fragrance dispenser for insertion in an automobile cigarette lighter socket.

U.S. Pat. No. Des. 315,789 and 4,968,456 to Muderlak disclose an electrical air freshener design and an electrical air freshener for automobiles.

U.S. Pat. No. 4,111,655 to Quincey discloses electrically operated air fresheners.

U.S. Pat. No. 5,136,684 to Lonker discloses a heating device for volatilization of fragrant gel.

Lastly, U.S. Pat. No. 5,171,485 to Ryan discloses a scent emitting device for automobiles.

In this respect, the automobile plug-in air fresheners according to the present invention substantially depart from the conventional concepts and designs of the prior art, and in doing so provides an apparatus primarily developed for the purpose of freshening the air of vehicles with devices plugged in to a cigarette lighter.

Therefore, it can be appreciated that there exists a continuing need for new and improved automobile plug-in air fresheners which can be used for freshening the air of vehicles with devices plugged in to a cigarette lighter. In this regard, the present invention substantially fulfills this need.

SUMMARY OF THE INVENTION

In view of the foregoing disadvantages inherent in the known types of air fresheners now present in the prior art, the present invention provides improved automobile plug-in air fresheners. As such, the general purpose of the present invention, which will be described subsequently in greater detail, is to provide new and improved automobile plug-in air fresheners and method which have all the advantages of the prior art and none of the disadvantages.

To attain this, the present invention essentially comprises a new and improved automobile plug-in air freshener comprising, in combination, a main body portion in a cylindrical configuration having an open outboard end and a closed inboard end and positionable along a horizontal axis in a cigarette lighter opening of a vehicle. An extension portion has a cone shaped interior component positioned outboardly of the open end of the cylinder with an interior edge in a cylindrical configuration positioned over the outboard end of the main body portion with an exterior component in a rectangular configuration constituting a housing with an opened inboard end and louvers at the outboard end and a slot along an upper intermediate extent. A generally planar refill container in a rectangular configuration is removably positionable within the slot of the rectangular housing, the refill container having a fragrance therein activated by heat. A heating element is located within the main body portion adjacent to the outboard open end adapted to heat the fragrance within the refill cartridge for disseminating a fragrance and freshening the adjacent air. Electrical components for energizing the heater comprise an electrical probe extending outboardly from the closed inboard end of the main body portion with a spring to urge the probe outwardly and with a wire extending therefrom to the heater and a resilient electrical contact extending radially from one cylindrical wall of the main body portion with a wire extending to the heater. A switch in the electrical wire between the resilient contact and the heater comprises a first contact element mounted within the interior surface of the main body portion adjacent to the outboard end and a corresponding electrical contact element mounted in the radially outward face of the interior edge of the extension portion, the contacts rotatably movable from an in-contact closed orientation and an out-of-contact orientation through the rotation of the cone shaped exterior component with respect to the cylindrical housing.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide new and improved automobile plug-in air fresheners which have all the advantages of the prior art air fresheners and none of the disadvantages.

It is another object of the present invention to provide new and improved automobile plug-in air fresheners which may be easily and efficiently manufactured and marketed.

It is further object of the present invention to provide new and improved automobile plug-in air fresheners which are of durable and reliable constructions.

An even further object of the present invention is to provide new and improved automobile plug-in air fresheners which are susceptible of a low cost of manufacture with regard to both materials and labor, and which accordingly are then susceptible of low prices of sale to the consuming public, thereby making such automobile plug-in air fresheners economically available to the buying public.

Still yet another object of the present invention is to provide new and improved automobile plug-in air fresheners which provide in the apparatuses and methods of the prior art some of the advantages thereof, while simultaneously overcoming some of the disadvantages normally associated therewith.

Still another object of the present invention is to freshen the air of vehicles with devices plugged into a cigarette lighter.

Lastly, it is an object of the present invention to provide a new and improved automobile plug-in air freshener with a main body portion in a cylindrical configuration having an open outboard end and a closed inboard end and positionable along a horizontal axis in a cigarette lighter opening of a vehicle. An extension portion has a cone shaped interior component positioned outboardly of the open end of the cylinder with an interior edge in a cylindrical configuration positioned over the outboard end of the main body portion with an exterior component in a rectangular configuration constituting a housing with an opened inboard end and louvers at the outboard end and a slot along an upper intermediate extent. A generally planar refill container in a rectangular configuration is removably positionable within the slot of the rectangular housing, the refill container having a fragrance therein activated by heat. A heating element is located within the main body portion adjacent to the outboard open end adapted to heat the fragrance within the refill cartridge for disseminating a fragrance and freshening the adjacent air.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a plan view of the automobile plug-in air freshener shown in FIG. 3.

FIG. 4 is a cross sectional view taken along line 4—4 of FIG. 3.

The same reference numerals refer to the same parts throughout the various Figures.

DESCRIPTION OF THE PREFERRED EMBODIMENT

Figure 1:
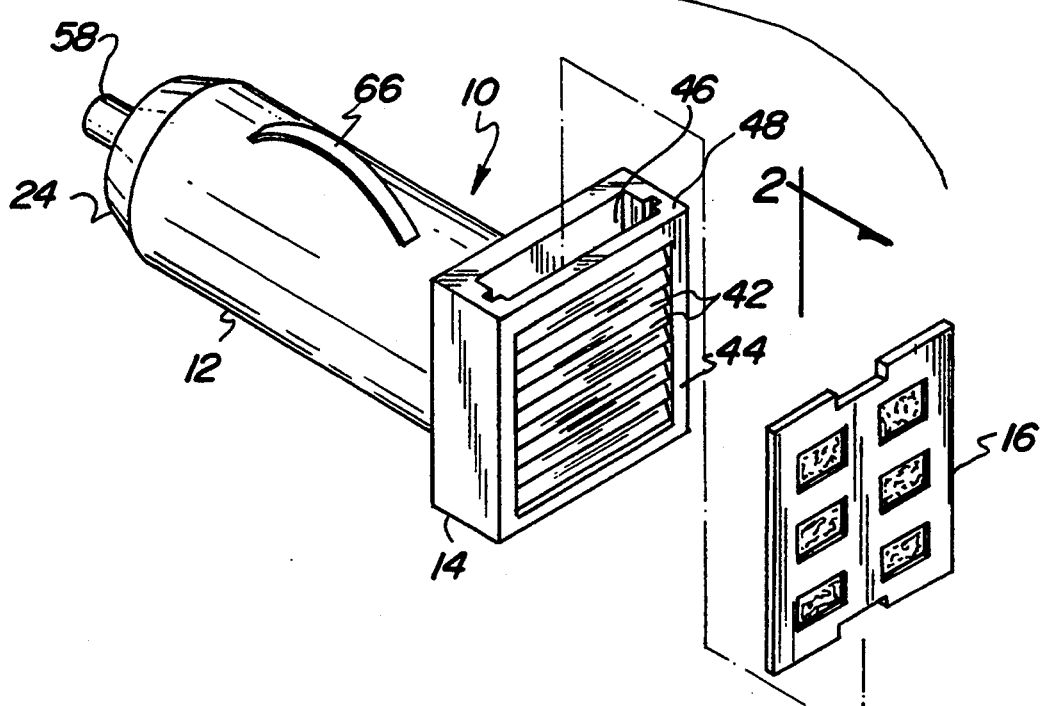
FIG. 1 is an exploded perspective view of the preferred embodiment of the automobile plug-in air freshener constructed in accordance with the principles of the present invention.
Figure 2:
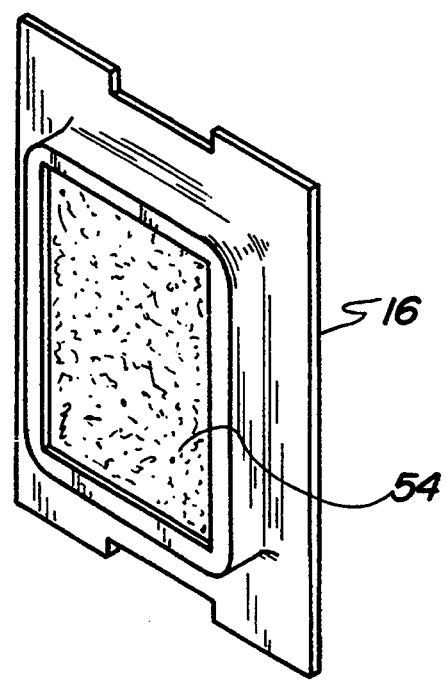
FIG. 2 is a rear perspective view of the refill cartridge taken along line 2—2 of FIG. 1 looking in the direction of the arrow.
Figure 5:
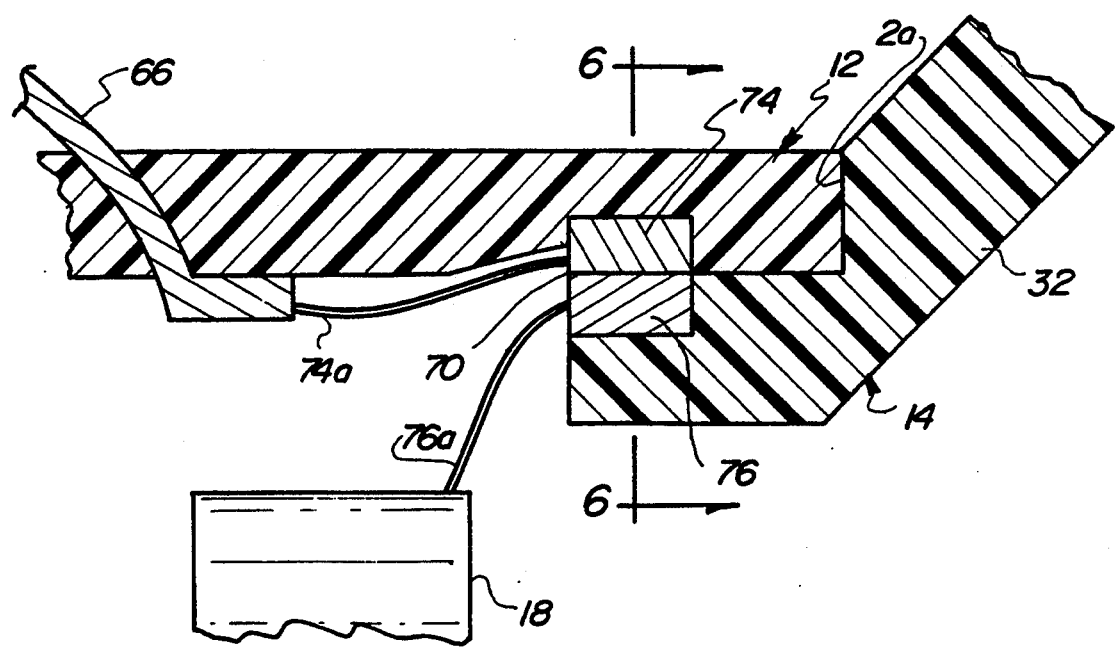
FIG. 5 is a enlarged view of the contact region shown in FIG. 4 and designated by the circle marked by numeral 5.
Figure 6:
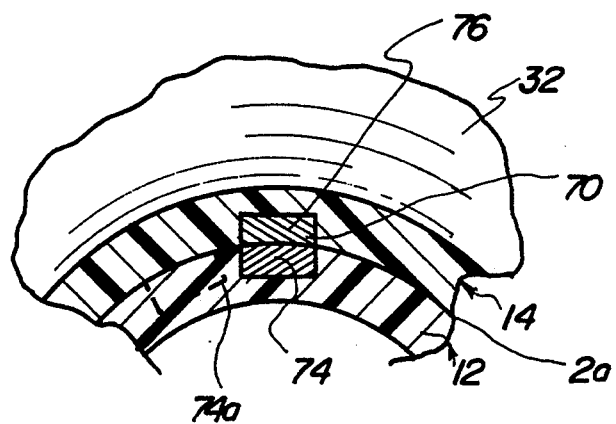
FIG. 6 is a cross sectional view of the contact taken along line 6—6 of FIG. 5.

With reference now to the drawings, and in particular to FIG. 1 thereof, the preferred embodiment of the new and improved automobile plug-in air fresheners embodying the principles and concepts of the present invention and generally designated by the reference numeral 10 will be described.

Specifically, it will be noted in FIGS. 1 through 6 there is shown the new and improved automobile plug-in air freshener. In its broadest of terms the device 10 includes a main body portion 12, an extension portion 14, a cartridge 16, a heater 18, and electrical components therebetween.

More specifically, the main body portion is in a cylindrical configuration. It has an open outboard end 22 and a closed inboard end 24. The main body portion is positionable along a horizontal axis and is adapted to be located in a cigarette lighter socket of a vehicle such as an automobile, truck, recreational vehicle, boat or the like.

The second portion of the device is the extension portion 14 rotatably mounted on the end 22 of body portion 12. The extension portion includes a cone shaped intermediate component 32 extending outboardly of the open end of the main body portion. A housing 36 is formed at the outboard end of the intermediate component. It is shaped in a rectangular configuration. It has an opened inboard end 40 and louvers 42 at the outboard end 44. A slot 46 is formed along an upper extent 48.

The third portion of the device is a planar refill container or cartridge 16. The cartridge is in a rectangular configuration. It is removably positionable within the slot to be located in the rectangular housing. It is adapted to be provided with a fragrance material 54 which emits a pleasant scent when heated.

A heating element 18 is located within the main body portion. It is positioned adjacent to the outboard open end. It is adapted to heat the fragrance material 54 within the refill cartridge 16 for disseminating a fragrance and freshen the adjacent air within the vehicle in which it is utilized. Electrical components within the device are configured for energizing the heater. Such components comprise an electrical probe 58. The probe extends outwardly from the closed inboard end 24 of the main body portion 12. A spring 60 is provided to urge the probe inboardly into contact with an electrical component of the cigarette lighter socket. A wire 62 extends therefrom to a terminal of the heater. The second contact is a resilient electrical contact 66. This contact extends radially outwardly from one cylindrical wall of the main body portion 12 to the heater. Its bowed surface is in contact with the cylindrical interior of a cigarette lighter socket from which it receives electrical current.

A switch 70 is also employed as an electrical component of the device 10. Such contact is located in the electrical line between the resilient contact 66 and the heater 18. The switch 70 comprises a first contact element 74 mounted within the interior surface of the main body portion 12 adjacent to its outboard end. A corresponding electrical contact 76 is located at the radially outward surface of the extension portion at its inboard end. The contacts are rotatably movable between an in-contact closed orientation and an out-of-contact open orientation through the rotation of the extension portion 14 with respect to the main body portion 12. Simple rotation of the contacts 74 and 76 through the rotation of their supporting members acts to energize and de-energize the heater for activating and inactivating the scent. Note the solid and dotted line showings in FIG. 6.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved automobile plug-in air freshener comprising, in combination:
   a hollow main body portion in a cylindrical configuration having an open outboard end and a closed inboard end and positionable along a horizontal axis in a cigarette lighter opening of a vehicle;
   a hollow extension portion having a cone shaped interior component rotatably positioned on the main body portion outboardly of the open end thereof with an interior edge in a cylindrical configuration positioned in the open outboard end of the main body portion and an exterior component in a rectangular configuration constituting a housing with an opened inboard end communicating with said main body portion and louvers at the outboard end and a slot along an upper intermediate extent;
   a generally planar refill container in a rectangular configuration removably positionable within the slot of the rectangular housing, the refill container containing a fragrance substance therein activatable by heat;
   a heater located within the main body portion adjacent to the outboard open end adapted to heat the fragrance substance within the refill cartridge for disseminating a fragrance and freshening the adjacent air;
   electrical components for energizing the heater comprising a electrical probe extending outwardly from the closed inboard end of the main body portion with a spring to urge the probe outwardly and with a wire extending therefrom to a terminal of the heater and a resilient electrical contact extending radially from cylindrical wall of the main body portion with a wire extending to the outer terminal of the heater; and
   a switch in the electrical wire between the resilient contact and the heater comprising a first contact element mounted within the interior surface of the main body portion adjacent to the outboard end and a corresponding electrical contact element mounted in the radially outward face of the interior edge of the extension portion, the contacts rotatably movable from an in-contact closed orientation and an out-of-contact orientation through the rotation of the extension portion with respect to the main body portion.

2. A vehicle plug-in air freshener comprising:
   a hollow main body portion in a cylindrical configuration having an open outboard end and a closed inboard end and positionable along a horizontal axis in a cigarette lighter socket of a vehicle;
   a hollow extension portion rotatably mounted in the main body portion having a cone shaped interior component positioned outboardly of the open end of the main body portion with an interior edge in a cylindrical configuration in the open outboard end of the main body portion and exterior component constituting a housing with an open inboard end communicating with the open end of said main body portion and louvers at the outboard end and a slot along an upper intermediate extent;
   a generally planar refill container removably positionable within the slot of the housing, the refill container having a fragrance substance therein activatable by heat;
   a heating element located within the main body portion adjacent to the outboard open end thereof adapted to heat the fragrance substance within the refill cartridge for disseminating a fragrance and freshening the adjacent air;
   electrical components for energizing the heater comprising an electrical probe extending outwardly from the closed inboard end of the main body portion with a spring to urge the probe outwardly and with a wire extending therefrom to a terminal of the heater and a resilient electrical contact extending radially from one cylindrical wall of the main body portion with a wire extending to the outer terminal of the heater; and
   a switch in the electrical wire between the resilient contact and the heater comprising a first contact element mounted within the interior surface of the main body portion adjacent to the outboard end and a corresponding electrical contact element mounted in the radially outward face of the interior edge of the extension portion, the contacts rotatably movable from an in-contact closed orientation and an out-of-contact orientation through the rotation of the cone shaped extension portion with respect to the main body portion.

* * * * *